United States Patent [19]

Corley

[11] Patent Number: 5,147,953

[45] Date of Patent: Sep. 15, 1992

[54] DIALKYLIDENECYCLOBUTANE/BISIMIDE COMPOSITIONS

[75] Inventor: Larry Steven Corley, Houston, Tex.

[73] Assignee: Shell Oil Company, Houston, Tex.

[21] Appl. No.: 733,947

[22] Filed: Jul. 22, 1991

[51] Int. Cl.$^5$ ............................................. C08F 12/32
[52] U.S. Cl. .................................................... 526/262
[58] Field of Search ................................. 526/262, 308

[56] References Cited

U.S. PATENT DOCUMENTS

| | | | |
|---|---|---|---|
| 4,645,814 | 2/1987 | Grabbs | 526/308 |
| 4,730,030 | 3/1988 | Hahn et al. | 526/262 |
| 4,927,907 | 5/1990 | Corley | 528/322 |
| 4,973,636 | 11/1990 | Gorley | 526/262 |

OTHER PUBLICATIONS

Godt et al., "Double-Stranded Molecules", *Angew. Chem. 28, 1680–1682 (1989)*.

*Primary Examiner*—Paul R. Michl

[57] ABSTRACT

A composition comprising a 1,2-dialkylidenecyclobutane such as 1,2-dimethylenecyclobutane and a polyimide such as a bismaleimide can be thermally cured to a tough copolymer having a high glass transition temperature and low water absorbance.

24 Claims, No Drawings

DIALKYLIDENECYCLOBUTANE/BISIMIDE COMPOSITIONS

BACKGROUND OF THE INVENTION

This invention relates to thermosettable resin compositions. In one embodiment, the invention relates to copolymers of a 1,2-dialkylidenecyclobutane and a bisimide. In a preferred embodiment, the invention relates to toughened bismaleimide resins.

Advanced composites are high-performance materials made up of a fiber-reinforced thermoplastic or thermosettable material. Thermosettable materials useful in advanced composites applications must meet a set of demanding property requirements. For example, such materials optimally have good high-temperature properties such as high (above 200° C.) cured glass transition temperature and low (less than 3%) water absorbance at elevated temperature. Such materials also exhibit high toughness, as reflected in a Mode I fracture toughness above 2 MPa.m$^{\frac{1}{2}}$. For ease of processing in preparing adhesives and prepregs for composite parts, the uncured material will ideally have a low (below 120° C.) melting temperature.

Examples of thermosettable materials useful in advanced composites include epoxy resins and bismaleimide resins. Epoxy resins have good processing properties, but generally have relatively low glass transition temperatures and unacceptable high-temperature water absorbance.

Bismaleimide resins have superior high-temperature properties but are very brittle and further tend, because of their high softening points, to require solvents in order to be readily processable. In addition, standard cured bismaleimide resins tend to have high (in the 5–7% range) 93° C. water absorption. Standard olefinic chain extenders for bismaleimides (such as bis-allylphenols) give rates of chain extension which are not significantly higher than the rates of the subsequent crosslinking reactions, making it difficult to use such materials to obtain the high molecular weight between crosslinks needed for very high toughness. Certain bis-benzocyclobutene crosslinkers for bismaleimides give high toughness, but these monomers are quite expensive to prepare, involving multistep syntheses from the nearest commercially available material.

It is thus an object of the invention to provide new thermoset resin materials. In one aspect, it is an object of the invention to provide comomomers which provide low-melting bismaleimides which cure to high-Tg, tough resins having low water absorbance.

SUMMARY OF THE INVENTION

According to the invention, a composition is provided comprising a 1,2-dialkylidenecyclobutane and a polyimide. In one embodiment, the invention composition is a copolymer product of thermally-initiated copolymerization of a difunctional bismaleimide and from about 0.6 to about 2.5 moles, per mole of the bismaleimide, of a 1,2-dialkylidenecyclobutane. The invention copolymers have superior toughness, exhibit low water absorbance, and can be melt-processed for composites and adhesives applications.

DETAILED DESCRIPTION OF THE INVENTION

The invention composition includes a polyimide. Preferred polyimides are N,N'-bisimides of unsaturated dicarboxylic acids which can be represented by the formula

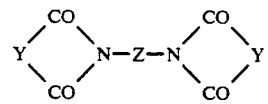

in which Y is a substituted or unsubstituted divalent group containing at least 2 carbon atoms, preferably 2 to 6 carbon atoms, and a carbon-carbon double bond, and Z is a divalent group containing at least 1 and generally about 1 to 40 carbon atoms. Z can be aliphatic, cycloaliphatic, aromatic or heterocyclic. A preferred class of bisimides comprises bismaleimides derived from aromatic amines and can be represented by the formula

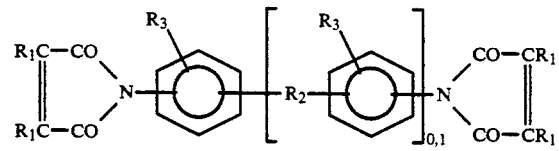

in which each $R_1$ is selected independently from H, $C_{1-2}$ alkyl or halide; $R_2$ is selected from divalent hydrocarbon radicals containing from about 1 to about 10 carbon atoms, —O—, —SO$_2$—, —COO—, —CONH—, —CO— and —S—; and each $R_3$ is selected independently from H, $C_{1-3}$ alkyl and halide. The aromatic rings may alternatively be heterocyclic.

Examples of such bisimides include
1,2-bismaleimidoethane
1,6-bismaleimidohexane
1,3-bismaleimidobenzene
1,4-bismaleimidobenzene
2,4-bismaleimidotoluene
4,4'-bismaleimidodiphenylmethane
4,4'-bismaleimidodiphenylether
3,3'-bismaleimidodiphenylsulfone
4,4'-bismaleimidodiphenylsulfone
4,4'-bismaleimidodicyclohexylmethane
3,5-bis(4-maleimidophenyl)pyridine
2,6-bismaleimidopyridine
1,3-bis(maleimidomethyl)cyclohexane
1,3-bis(maleimidomethyl)benzene
1,1-bis(4-maleimidophenyl)cyclohexane
1,3-bis(dichloromaleimido)benzene
4,4'-biscitraconimidodiphenylmethane
2,2-bis(4-maleimidophenyl)propane
1-phenyl-1,1-bis(4-maleimidophenyl)ethane
α,α-bis(4-maleimidophenyl)toluene
3,5-bismaleimido-1,2,4-triazole
and various N,N'-bismaleimides disclosed in U.S. Pat. Nos. 3,562,223, 4,211,860 and 4,211,861. Bismaleimides can be prepared by methods known in the art, as described in U.S. Pat. No. 3,018,290, for example.

Also included in the bismaleimide resins are imide oligomers according to the formula

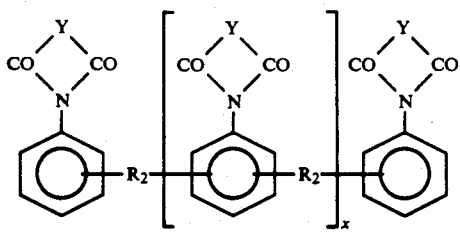

in which x is a number within the range of about 0 to about 3.

The preferred bisimide resin is N,N'-4,4'-diphenylmethane bismaleimide. The bisimide can contain various additives and modifiers as processing aids. The bisimide resin component can be a reaction product or prepolymer of a bisimide and an effective chain-extending agent such as an amine group-containing compound. Suitable amine group-containing compounds include diamines and polyamines represented by the general formula $(H_2N)_nQ$ or $(RNH)_nQ$ and aminophenols represented by the general formula $(NH_2)_nQ(OH)_n$ or $(RNH)_nQ(OH)_n$, in which Q is a divalent aromatic or alicyclic group and n is a number such that the average number of amine hydrogens per molecule in the amine mixture falls between about 1.95 and 2.5. Examples include bis(4-(N-methylamino)phenyl)methane, N,N'-dimethyl-1,3-diaminobenzene and the like. Such reaction products can be prepared by methods known in the art, such as contacting about 0.1 to about 0.8 mole of the chain-extending agent per mole of the bisimide in an organic solvent at a temperature of about 40° to 250° for a time of about 5 minutes to 5 hours. The bisimide can be, for example, a hydrazide-modified bismaleimide as described in U.S. Pat. Nos. 4,211,860 and 4,211,861. Suitable N,N'-unsaturated bismaleimide resins are commercially available from Technochemie GmbH as Compimide ® resins, for example.

The invention composition includes a 1,2-dialkylidenecyclobutane, including those which can be described by the structural formula

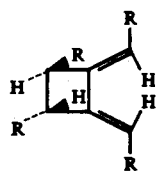

in which each R is selected independently from hydrogen, $C_{1-10}$ alkyl, halo, aryl, alkoxy, aryloxy, alkylthio, arylthio and dialkylamino. The presently preferred 1,2-dialkylidenecyclobutane, because of the superior properties of a bisimide copolymer prepared therewith, is 1,2-dimethylenecyclobutane, which is defined by the above formula when each R is hydrogen.

The dialkylidenecyclobutane (DACB) and the polyimide are combined in the molar ratios which produce the desired property modification to the polyimide, within the range of about 99:1 to about 1:99, generally from about 25:75 to about 75:25. For enhanced toughness in a cured bisimide, the molar ratio of DACB: bisimide will generally be within the range of about 0.6:1 to about 2.5:1, preferably about 0.8:1 to about 1.5:1, most preferably about 0.9:1 to about 1.1:1.

PREPARATION OF DIALKYLIDENECYCLOBUTANE

In general, dialkylidenecyclobutanes can be prepared by the thermal dimerization of the corresponding allenes in a recirculating hottube reactor. Specifically, the process will generally be carried out by circulating a stream of gaseous allene through a tube reactor at 450°-600° C. with a residence time in the hot zone of 0.1 to 10 seconds. Downstream from the hot zone, the stream is cooled sufficiently to condense the dialkylidenecyclobutane. Unchanged allene (combined with a fresh makeup stream) is recirculated back to the hot zone by a pump. Such a process is described for 1,2-dimethylenecyclobutane in Chernykh et al., *Nefteperenab. Neftekhim.*, 1981 (7), 48–50. Synthesis of 1,2-dimethylenecyclobutane is also illustrated in Example 1 herein. The allene starting material can be produced by pyrolysis of isobutylene or by isolation from a hydrocarbon mixture such as a refinery cracker stream.

PREPARATION OF POLYIMIDE/DIALKYLIDENECYCLOBUTANE COPOLYMERS

The polyimide and the 1,2-dialkyleneidcyclobutane monomers may be combined in any manner desired, such as melt, solution or powder blending. The preferred technique, when sufficiently large quantities of monomers are used, involves heating a mixture of the solid polyimide and the liquid 1,2-dialkylidenecyclobutane with stirring until the mixture becomes a homogeneous melt. The melt may optionally be held at temperatures above about 140° C. for desired periods of time in a process of prepolymerization to increase the crystallization resistance of the melt and/or to increase its viscosity to desired levels. The mixture can then be poured directly into a mold for polymerization, or it can be cooled for later polymerization. For small quantities of monomers, however, excessive amounts of the dialkylidenecyclobutane may volatilize during the melt reaction, upsetting the desired stoichiometric balance. In these cases, it is preferable for the comonomer mixture to be processed in a two-step process in which the imide/DACB mixture is reacted in a solvent, with the solvent then evaporated and the adduct melted and cured to solid polymer without solvent.

Polymerization is effected by heating the mixture to a temperature effective to initiate opening of the cyclobutene ring (formed by the initial Diels-Alder reaction of the diene group of the dialkylidenecyclobutane with the dieneophilic double bond) to form a transient diene which rapidly reacts with available maleimide groups. This temperature is generally at least about 180° C., preferably about 210° to about 350° C., held for a time of about 2 hours or more (with the required cure time dependent on the temperaturestaging program used).

In order to achieve the superior properties exhibited by the invention copolymers, a mixture of the monomers is heated at a temperature near (within 15° C. below) or above the ultimate, or fully-cured, glass transition temperature of the copolymer ($Tg_u$) for a time sufficient to produce essentially complete reaction of the monomers. "Essentially complete" reaction of the monomers has been reached when no further reaction exotherm is observed by differential scanning calorimetry (DSC) upon heating the copolymer. The time of the heat treatment, or "post-cure," will vary depending upon the monomers, the degree of pressure applied and any precuring of the monomer mixture at temperatures lower than about ($Tg_u$-15° C.). Preferably, this postcure is at or above the ultimate Tg, most preferably at least 20° C. above $Tg_u$, but will always be at a temperature lower than the temperature at which degradation of the copolymer will occur at significant rates.

THE COPOLYMERS

The cured imide/alkylidenecyclobutane copolymers are characterized by glass transition temperatures (dynamic mechanical) generally above about 200° C., Mode I toughness (ASTM E 399-83 using $1 \times 1 \times \frac{1}{8}$" samples) greater than about 2.0 MPa . $m^{\frac{1}{2}}$, and water absorption (93° C.) less than about 3%. Methyl ethyl ketone absorption (room temperature) is frequently less than 1% in the preferred species.

The copolymers are useful in adhesives, coatings and as resin matrices for composites in aerospace and electronics applications, including large structural parts and circuit boards. Based on their long shelf life and relatively low melting point, some of the uncured mixtures are useful for making tacky prepregs which can then be molded into composites. They are also suitable for low-solvent or solventless liquid resin processing methods such as filament winding, resin transfer molding and pultrusion if the mixtures are heated to provide sufficiently low viscosity for fiber impregnation. If the monomer mixtures are prepared so as to avoid crosslinking, they can also be used as injection-moldable thermoplastics.

Electrical applications for the invention compositions include encapsulation of electronic devices and electrical lamination for circuit board manufacture. In encapsulation, the composition will usually be combined, generally by melt-blending, with a suitable inert filler such as particulate silica. For lamination, the composition will be applied, in organic solution or in a solventless melt, to a suitable reinforcement such as glass fiber, and partially cured to form an electrical prepreg, which will subsequently be fabricated into a fully-cured laminate.

For preparation of reinforced laminate materials, a fibrous substrate of glass, carbon, quartz, poly(p-phenyleneterephthalamide), polyester, polytetrafluoroethylene, poly(p-phenylenebenzobisthiazole), boron, paper or like material, in chopped, mat or woven form, is impregnated with a bisimide/dialkylidenecyclobutane composition in molten or solution form. A prepreg is formed by heating the impregnated substrate in an oven at a temperature sufficient to remove the solvent and to partially cure without gelation, or "B-stage," the resin system, generally about 180° C. to about 230° C., preferably about 200° to about 220° C., for a time of up to about 2 hours, preferably about 10 to about 40 minutes. A laminate is fabricated by subjecting a set of layered prepregs to conditions effective to cure the resins and to integrate the prepregs into a laminated structure. The laminate can optionally include one or more layers of a conductive material such as copper.

Laminating generally involves subjecting the prepregs to a temperature above about 200° C., preferably from about 210° to about 350° C., for a time of at least about 1 hour, at a pressure within the range of about 50 to about 500 psi.

For some laminating applications, it may be advantageous to heat treat, or upstage, the monomer mixture prior to application to a laminating substrate, particularly if the mixture will be stored prior to use. Suitable heat treatment involves subjecting the mixture to an elevated temperature for a time sufficient to cause sufficient reaction and viscosity increase to inhibit crystallization of either or both monomers from the mixture upon storage, but not sufficient to gel the composition. Such heat treatment conditions generally include a temperature of at least about 140° C., preferably about 170° to about 200° C., for a time of at least about 10 minutes, preferably about 12 to about 90 minutes. The resulting mixture will be less tacky and less susceptible to crystallization of the components with storage.

EXAMPLE 1

Preparation of 1,2-Dimethylenecyclobutane

A recirculating apparatus for the thermal dimerization of allene was designed as follows. The heated reactor was a quartz tube 23 mm in internal diameter in an electric tube furnace. The heated zone was 30 cm long. Downstream from the reactor was a cold trap containing a cooling fluid at approximately −35° C. above a flask which held condensed allene dimer. Downstream from the first trap was a second trap filled with dry ice in dichloromethane, guarding the outlet to the system (through an oil bubbler) to condense any allene which otherwise could have escaped from the system. Condensed allene from this second trap fell into a liquid allene reservoir. Sufficient heat was applied to the resorvoir to keep the allene at gentle reflux between the reservoir and the second cold trap. A tube from the vapor space above the second allene reservoir led to a diaphragm pump which recirculated the allene back into the hot tube. A makeup stream of fresh allene from a cylinder was also introduced into the loop just upstream from the recirculation pump.

The hot tube contained a thermal well at its center which extended the length of the tube. A thermocouple was positioned in the well at the outlet of the hot zone. In the following reaction runs, the thermocouple temperature was kept at approximately 490° C. (This required some variation in furnace wall temperature during the reactions). The system was purged with nitrogen and allene was slowly introduced until a substantial amount had accumulated in the allene reservoir, with the allene supply then shut off. The accumulated allene was allowed to recirculate through the loop during the rest of the day as it was slowly converted into dimer which accumulated in the reservoir under the first trap. At the end of the day, the power to the furnace was turned off, the system was allowed to cool, and the accumulated dimer was poured into a bottle and weighed. Approximately 0.1 g of phenothiazine was placed in each bottle of dimer to inhibit polymerization of the 1,2-dimethylenecyclobutane. The crude dimer was then analyzed by gas chromatography for peaks corresponding to two allene dimers, 1,2-dimethylenecyclobutane (1,2-DMCB) and 1,3-dimethylenecyclobutene (1,3-DMCB), and a component shown by mass spectrometry to have a molecular formula of $C_9H_{12}$ (an allene trimer). Data from these six hot tube reaction runs are shown in Table 1.

TABLE 1

| Reaction # | Reaction time, hr. | Allene used, g | Crude dimer produced, g | Crude yield, % | GC analysis | | |
|---|---|---|---|---|---|---|---|
| | | | | | 1,3-DMCB, % | 1,2-DMCB, % | $C_8H_{12}$ peak, % |
| 1 | 6.5 | 99.2 | 18.99 | 19.1 | 13.3 | 70.0 | 9.7 |
| 2 | 7.3 | 45.2 | 23.98 | 53.1 | 11.1 | 72.2 | 10.2 |
| 3 | 7.8 | 43.4 | 19.76 | 45.5 | 13.9 | 63.4 | 12.2 |
| 4 | 6.9 | 36.5 | 15.19 | 41.6 | 12.4 | 66.4 | 10.9 |
| 5 | 7.0 | 33.8 | 12.54 | 37.1 | 12.3 | 72.7 | 8.4 |
| 6 | 5.0 | 62.8 | 11.15 | 14.3 | 11.9 | 72.3 | 7.4 |

The products of the six runs in Table 1 were combined in a 250-mL flask and distilled at atmospheric pressure under nitrogen in a distillation head with an integral vacuum-jacketed Vigreux column. The total charge weight was 96.41 g. After a small forecut (4.77 g), a main cut of 63.3 g was collected at 73°–74° C. Gas chromatographic analysis of the main cut showed a 1,2-dimethylenecyclobutane content of 84.8% and a 1,3-dimethylenecyclobutane content of 12.5%. The chromatogram also contained several other small peaks. Approximately 0.5 g of phenothiazine was added to the main cut to inhibit polymerization. This main cut was used in Example 2 to make castings.

EXAMPLE 2

Into a glass beaker were weighed 230.9 g of 4,4-bismaleimidodiphenylmethane, 38.9 g of 2,4-bismaleimidotoluene, 36.9 g of 1,3-bismaleimidobenzene, and 0.9315 g of phenothiazine (added as an inhibitor to prevent radical polymerization of the bismaleimides on heating). The bismaleimide mixture was used for ease of processing, in order to prevent the bismaleimide or bismaleimide/1,2-dimethylenecyclobutane adduct from crystallizing from the melt or solution. The mixture was heated in an oil bath to 200° C., stirred until homogeneous, and allowed to cool to room temperature, solidifying to an amorphous mass. The mass was then broken up into small pieces and co-cured with the main distillation cut from Example 1.

Five mixtures were prepared as follows. To a 100 mL flask fitted with a condenser were added 20.04 g of the above bismaleimide mixture, the amount indicated in Table 2 below of the main distillation cut, approximately 0.06–0.07 g of Monsanto PC-1344 defoamer (an acrylic oligomer, added to prevent excessive foaming during vacuum degassing and to enable the preparation of void-free castings) and 60 g of dichloromethane. The mixtures were allowed to react overnight (or longer) with stirring at room temperature and were then refluxed for 5 hours. The mixtures were then poured into 125 mL Erlenmeyer flasks with a vacuum connection. The flasks were placed in a 150° C. oil bath and the contents were swirled as solvent, 1,3-dimethylenecyclobutane and other volatile unreacted materials were removed, first at atmospheric pressure and then under mechanical pump vacuum for a few minutes until bubbling had essentially stopped. The degassed molten mixtures were then poured into a two-piece rectangular stainless steel mold with a 1/16" thick cavity, with the mold parts separated by an airtight rubber gasket such that the mold could be pressurized during cure. The mold was then placed into an oven and pressurized with nitrogen to 750 kPa (about 95 psig) and the systems were cured for one hour at 150° C., one hour at 180° C., one hour at 210° C., 30 minutes at 230° C., 30 minutes at 250° C., 30 minutes at 270° C. and one hour at 290° C. Properties of the castings are shown in Table 2.

TABLE 2

| Experiment # | 1 | 2 | 3 | 4 | 5 |
|---|---|---|---|---|---|
| Bismaleimide mixture, g | 20.04 | 20.04 | 20.04 | 20.04 | 20.04 |
| Main distillation cut from Example 1, g | 3.78 | 4.53 | 5.68 | 6.80 | 8.50 |
| Monsanto PC-1344 defoamer, g | 0.0628 | 0.0653 | 0.064 | 0.064 | 0.0631 |
| 1,2-DMCB/BMI molar ratio | 0.67 | 0.80 | 1.00 | 1.20 | 1.50 |
| Rheometrics tan δ peak, °C. | ≧400 | ≧388 | 319 | 309 | 309 |
| R.T. dry flexural (ASTM D-790): | | | | | |
| Yield strength, MPa | 77 ± 15 | 100 ± 3 | 94 ± 1 | 97 ± 2 | 94 ± 1 |
| Tangent modulus, GPa | 3.45 ± 0.05 | 3.27 ± 0.04 | 3.10 ± 0.06 | 3.17 ± 0.01 | 3.15 ± 0.04 |
| Break elongation, % | 2.5 ± 0.7 | >6.5 | >6.5 | >6.1 | >6.0 |
| 93° C. wet flexural (ASTM D-790): | | | | | |
| Yield strength, MPa | 77 ± 1 | 71 ± 1 | 37 ± 1[a] | 57 ± 3 | 60 ± 1 |
| Tangent modulus, GPa | 2.99 ± 0.12 | 2.79 ± 0.03 | 1.98 ± 0.28 | 2.63 ± 0.15 | 2.49 ± 0.04 |
| Break elongation, % | 3.0 ± 0.1 | >6.5 | 3.0 ± 0.2 | 4.8 ± 0.1 | 3.8 ± 0.4 |
| Compact tension fracture toughness, $K_Q$, MPa-m$^{\frac{1}{2}}$ (ASTM E399-83) | 0.76 | 1.24 ± 0.11 | 2.07 ± 0.08 | 2.87 ± 0.06 | 2.38 ± 0.05 |
| 93° C. H$_2$O pickup, %: | | | | | |
| 1 day | 2.04 | 2.08 | 2.52 | 2.02 | 2.02 |
| 2 weeks | 2.71 | 2.79 | 2.53[a] | 2.31 | 2.10 |
| Room temp. MEK pickup, %: | | | | | |
| 1 day | 0 | 0 | 0 | 0 | 0 |
| 2 weeks | 0 | 0 | 0 | 1.13 | 5.06 |
| Room temp. CH$_2$Cl$_2$ pickup, %: | | | | | |
| 1 day | 2.16 | 49.5 | 165 | 298 | >245 |
| 2 weeks | 60.7 | 87.5 | 165 | 273 | (disintegr.) |

[a]Sample appeared to contain many tiny voids after 2 week soak in 93° C. water.

One can see from Table 2 that all of the systems containing the diene from the main distillation cut of Example 1, over the range of DMCB/BMI molar ratios tested, have very high Tg values (>300° C.) and that many also have extremely high fracture toughness for a thermosetting polymer (>2 MPa.m$^{\frac{1}{2}}$). A number of the test samples, in the flexural test at room temperature, did not break at the maximum 6.5% elongation measurable by the test apparatus. By contrast, a casting prepared from the bismaleimide mixture alone was so brittle that it could not be satisfactorily machined into specimens for mechanical testing.

I claim:

1. A composition comprising
   (a) a polyimide having at least two dienophilic groups per molecule; and
   (b) a 1,2-dialkylidenecyclobutane which can be represented by the structural formula

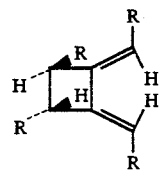

in which each R is selected independently from hydrogen, $C_{1-10}$ alkyl, halo, aryl, alkoxy, aryloxy, alkylthio, arylthio and dialkylamino.

2. The composition of claim 1 in which component (a) is present in an amount within the range of about 25 to about 75 mole percent, based on the moles of (a) and (b).

3. The composition of claim 2 in which component (a) is a bisimide.

4. The composition of claim 3 in which component (b) is 1,2-dimethylenecyclobutane.

5. The composition of claim 4 in which the molar ratio of the 1,2-dimethylenecyclobutane to the bisimide is within the range of about 0.8:1 to about 1.5:1.

6. The composition of claim 1 in which component (a) is a bismaleimide of an unsaturated dicarboxylic acid and component (b) is 1,2-dimethylenecyclobutane.

7. The composition of claim 6 which further comprises an effective amount of a free radical inhibitor for the bismaleimide.

8. The composition of claim 6 which further comprises a fibrous reinforcing agent.

9. The composition of claim 6 which further comprises particulate silica.

10. A polymeric composition comprising the product of contacting, at a temperature of at least about 180° C., monomers comprising
    (a) a bisimide of an unsaturated dicarboxylic acid and
    (b) a 1,2-dialkylidenecyclobutane.

11. The composition of claim 10 in which the molar ratio of the dialkylidenecyclobutane to the bisimide is within the range of about 0.8:1 to about 1.5:1.

12. The composition of claim 10 which has a glass transition temperature greater than about 200° C. and a Mode I fracture toughness greater than about 2.0 MPa.m$^{\frac{1}{2}}$.

13. The composition of claim 10 in which component (a) is a bismaleimide and component (b) is 1,2-dimethylenecyclobutane.

14. The composition of claim 13 which has a glass transition temperature greater than about 200° C. and a Mode I fracture toughness greater than about 2.0 MPa.m$^{\frac{1}{2}}$.

15. A prepreg comprising the composition of claim 1 and a fibrous substrate.

16. A process for preparing a copolymer comprising the steps of
    (a) preparing a mixture of a difunctional bisimide of an unsaturated dicarboxylic acid and from about 0.6 to about 2.5 moles, per mole of the difunctional bisimide, of a 1,2-dialkylidenecyclobutane which can be represented by the formula

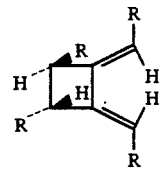

in which each R is selected independently from hydrogen, $C_{1-10}$ alkyl, halo, aryl, alkoxy, aryloxy, alkylthio, arylthio and dialkylamino; and
    (b) heating said mixture to a temperature within the range of about 200° to about 350° C. for at least about 1 hour.

17. The process of claim 16 in which the difunctional bismaleimide comprises bis(4-maleimidophenyl)methane.

18. The process of claim 17 in which the difunctional bismaleimide further comprises at least one of 2,4-bismaleimidotoluene and 1,3-bismaleimidobenzene.

19. A method for preparing a bisimide copolymer having a Mode I fracture toughness greater than 2 MPa.m$^{\frac{1}{2}}$ and a Tg greater than 200° C., the method comprising:
    (a) blending a bisimide monomer with from about 0.6 to about 2.5 moles, per mole of the bisimide monomer, of a 1,2-dialkylidenecyclobutane monomer which can be represented by the formula

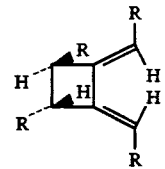

in which each R is independently selected from hydrogen, $C_{1-10}$ alkyl, halo, aryl, alkoxy, aryloxy, alkylthio, arylthio and dialkylamino; and
    (b) heating said monomer blend to a temperature of at least about ($Tg_u - 15°$ C.), where $Tg_u$ is the ultimate glass transition temperature of the 1,2-dialkylidenecyclobutane/bisimide copolymer, for a time sufficient for essentially complete reaction of the bisimide and the 1,2-dialkylidenecyclobutane monomers.

20. The method of claim 19 in which the bisimide comprises bis(4-maleimidophenyl)methane and the 1,2-dialkylidenecyclobutane comprises 1,2-dimethylenecyclobutane.

21. A copolymeric product of the process of claim 19.

22. The composition of claim 1 further comprising particulate silica.

23. The composition of claim 1 further comprising glass fibers.

24. An adhesive composition comprising the composition of claim 1.

* * * * *